US012673318B2

(12) United States Patent
Nakamura et al.

(10) Patent No.: US 12,673,318 B2
(45) Date of Patent: Jul. 7, 2026

(54) 1,3-BUTADIENE SYNTHESIS CATALYST, METHOD FOR PRODUCING SAME, AND METHOD FOR PRODUCING 1,3-BUTADIENE

(71) Applicant: Toyo Tire Corporation, Itami (JP)

(72) Inventors: Norihiko Nakamura, Itami (JP); Noritatsu Tsubaki, Toyama (JP); Guohui Yang, Toyama (JP)

(73) Assignee: TOYO TIRE CORPORATION, Itami (JP)

( * ) Notice: Subject to any disclaimer, the term of this patent is extended or adjusted under 35 U.S.C. 154(b) by 152 days.

(21) Appl. No.: 18/572,000

(22) PCT Filed: Jul. 29, 2021

(86) PCT No.: PCT/JP2021/028201
§ 371 (c)(1),
(2) Date: Dec. 19, 2023

(87) PCT Pub. No.: WO2023/007677
PCT Pub. Date: Feb. 2, 2023

(65) Prior Publication Data
US 2024/0359167 A1 Oct. 31, 2024

(51) Int. Cl.
*B01J 29/40* (2006.01)
*B01J 35/63* (2024.01)
(Continued)

(52) U.S. Cl.
CPC ........... *B01J 29/405* (2013.01); *B01J 35/633* (2024.01); *B01J 35/635* (2024.01); *B01J 35/638* (2024.01);
(Continued)

(58) Field of Classification Search
CPC ...... B01J 29/405; B01J 35/633; B01J 35/635; B01J 35/638; B01J 35/695; B01J 37/0018;
(Continued)

(56) References Cited

U.S. PATENT DOCUMENTS

2016/0145171 A1* 5/2016 Spannhoff ............. C01B 39/085
585/327
2022/0340435 A1* 10/2022 Hodgkins .............. B01J 35/617

FOREIGN PATENT DOCUMENTS

CN 109894144 A 6/2019
CN 111217656 A 6/2020
(Continued)

OTHER PUBLICATIONS

Yang et al., "Preparation of β zeolite with intracrystalline mesoporosity via surfactant-templating strategy and its application in ethanol-acetaldehyde to butadiene", Microporous and Mesoporous Materials, 2021, vol. 316, 110949, pp. 1-9, cited in ISR (9 pages).
(Continued)

*Primary Examiner* — Prem C Singh
*Assistant Examiner* — Francis C Campanell
(74) *Attorney, Agent, or Firm* — WHDA, LLP

(57) ABSTRACT

A catalyst according to an embodiment is a catalyst for synthesizing 1,3-butadiene from ethanol. The catalyst contains a porous silica support made of crystalline silica, Zn, and Zr, and has a multimodal pore size distribution with a peak pore size ($D_{micro}$) of 2 nm or less and a peak pore size ($D_{meso+macro}$) of more than 2 nm.

13 Claims, 4 Drawing Sheets

(51) Int. Cl.

| | |
|---|---|
| ***B01J 35/66*** | (2024.01) |
| ***B01J 37/00*** | (2006.01) |
| ***B01J 37/10*** | (2006.01) |
| ***C07C 1/24*** | (2006.01) |

(52) U.S. Cl.

CPC ......... *B01J 35/695* (2024.01); *B01J 37/0018* (2013.01); *B01J 37/10* (2013.01); *C07C 1/24* (2013.01); *C07C 2521/06* (2013.01); *C07C 2521/08* (2013.01); *C07C 2523/06* (2013.01)

(58) Field of Classification Search

CPC ......... B01J 37/10; B01J 29/7057; C07C 1/24; C07C 2521/06; C07C 2521/08; C07C 2523/06; C07C 2529/40; C07C 1/20

USPC .......................................................... 585/609

See application file for complete search history.

(56) References Cited

FOREIGN PATENT DOCUMENTS

| | | | |
|---|---|---|---|
| CN | 112479222 | A | 3/2021 |
| WO | 2013/125389 | A1 | 8/2013 |
| WO | 2014/198901 | A1 | 12/2014 |
| WO | 2014/199348 | A2 | 12/2014 |

OTHER PUBLICATIONS

International Search Report dated Sep. 21, 2021, issued in counterpart International Application No. PCT/JP2021/028201, w/English translation (6 pages).

Extended (Supplementary) European Search Report dated Mar. 25, 2025, issued in counterpart EP Application No. 21951877.6. (11 pages).

Imai, H. et al., Elucidation of the active site of zeolite catalysts containing transition metals for direct synthesis of butadiene from various carbon resources, Petrotech, vol. 42, No. 8, Aug. 1, 2018, p. 597-601, with English translation. (12 pages); cited in Extended European Search Report dated Mar. 25, 2025.

Smeets, V., et al., Hierarchical micro-/macroporous TS-1 zeolite epoxidation catalyst prepared by steam assisted crystallization, Microporous and Mesoporous Materials, Elsevier, vol. 293, Oct. 11, 2019. (7 pages); cited in Extended European Search Report dated Mar. 25, 2025.

Sun, M et al., A comparative study of hierarchically micro-meso-macroporous solid-acid catalysts constructed by zeolites nanocrystals synthesized via a quasi-solid-state crystallization process, Microporous and Mesoporous Materials, Elsevier, vol. 182, p. 122-135, Jan. 1, 2018. (11 pages); cited in Extended European Search Report dated Mar. 25, 2025.

Office Action dated Jul. 31, 2025, issued in counterpart CN Application No. 202180099364.8, with English translation. (19 pages).

Zheng, H., Study on 1,3-Butadiene Synthesis from Ethanol over Modified ZrO2/SiO2 Catalysts, Chinese Master's Theses Full-text Database, Engineering Science and Technology I, vol. 2, 2018, with English translation (37 pages); cited in CN Office Action dated Jul. 31, 2025.

Office Action dated Nov. 26, 2024, issued in counterpart JP Application No. 2023-537867, with English translation. (13 pages).

Office Action dated Nov. 13, 2025, issued in counterpart CN Application No. 202180099364.8, with English translation. (13 pages).

Office Action dated Mar. 23, 2026, issued in counterpart CN Application No. 202180099364.8, with English translation.(12 pages).

* cited by examiner

1,3-BUTADIENE SYNTHESIS CATALYST, METHOD FOR PRODUCING SAME, AND METHOD FOR PRODUCING 1,3-BUTADIENE

TECHNICAL FIELD

Embodiments of the present invention relate to a catalyst for synthesizing 1,3-butadiene from ethanol, a method for producing the same, and a method for producing 1,3-butadiene using the catalyst.

BACKGROUND ART 1,3-Butadiene is widely used as a raw material in the production of butadiene rubber (BR) and styrene-butadiene rubber (SBR). Currently, 1,3-butadiene is mainly produced by separation from the C4 fraction resulting from the production of ethylene by steam-cracking naphtha. In recent years, there has been a demand for the synthesis of 1,3-butadiene from non-petroleum raw materials. As such an alternative method, a synthesis method in which ethanol is directly converted into 1,3-butadiene has been proposed.

For example, in PTL 1, as a catalyst for obtaining butadiene through contact with ethanol, a catalyst containing a zeolite material having a $YO_2$-containing framework structure, in which at least part of Y contained in the framework structure is isomorphously substituted with element X, has been disclosed. Here, Y is preferably Si, Sn, Ti, Zr, or Ge, and X is preferably Zr, Ti, Sn, or Ta. PTL 1 also discloses that a zeolite material in which Y is Si, and X is Ti, may further contain Zn as a non-framework element.

In PTL 2, as a catalyst for obtaining 1,3-butadiene from ethanol, a catalyst obtained by kneading magnesium hydroxide, colloidal silica, zinc nitrate, and zirconium oxynitrate together with water, followed by calcination, ($ZnO/ZrO_2/MgO/SiO_2$) has been disclosed.

CITATION LIST

Patent Literature

PTL 1: WO2014/198901A1
PTL 2: WO2013/125389A1

SUMMARY OF INVENTION

Technical Problem

Direct conversion of ethanol into 1,3-butadiene is a promising route. However, the direct conversion is a complex reaction, requiring multifunctional catalysts having dehydrogenation sites, Lewis acid sites, and mild Bronsted sites. Nevertheless, with conventional catalysts, the yield of 1,3-buta diene is not necessarily high, and an improvement in the yield has been demanded.

An object of some embodiments of the invention is to provide a catalyst for 1,3-butadiene synthesis, which is capable of efficiently synthesizing 1,3-butadiene from ethanol, a method for producing the same, and a method for producing 1,3-butadiene using the catalyst.

Solution to Problem

The invention includes the following embodiments.

[1]A catalyst for 1,3-butadiene synthesis for synthesizing 1,3-butadiene from ethanol, containing a porous silica support made of crystalline silica, Zn, and Zr, the catalyst having a multimodal pore size distribution with a first peak pore size ($D_{micro}$) of 2 nm or less and a second peak pore size ($D_{meso+macro}$) of more than 2 nm.

[2] A method for producing 1,3-butadiene, including obtaining 1,3-butadiene from ethanol in the presence of a catalyst containing a porous silica support made of crystalline silica, Zn, and Zr, the catalyst having a multimodal pore size distribution with a first peak pore size ($D_{micro}$) of 2 nm or less and a second peak pore size ($D_{meso+macro}$) of more than 2 nm.

[3] In the above [1] or [2], the catalyst contains, as the Zn, ZnO supported on the silica support and, as the Zr, Zr that has interacted with silanol groups of the silica support.

[4] In any of the above [1] to [3], the catalyst is configured such that the micropore volume ($V_{micro}$) calculated by the t-plot method is 0.03 to 0.30 $cm^3/g$, and the mesopore volume ($V_{meso}$) calculated by the BJH method is 0.30 to 2.0 $cm^3/g$.

[5] In any of the above [1] to [4], the catalyst is configured such that the silica support has an MFI-type framework structure.

[6] In any of the above [1] to [5], the catalyst is configured such that the molar ratio Zn/Si of Zn to Si is 0.001 to 0.1, and the molar ratio Zr/Si of Zr to Si is 0.05 to 0.5.

[7] In any of the above [1] to [6], the catalyst is a catalyst obtainable by mixing a zirconium alkoxide, an orthosilicic acid ester, and a first template agent together with water to prepare a zirconium silicate precursor, and mixing the zirconium silicate precursor, a zinc salt, an orthosilicic acid ester, and a second template agent together with water, followed by hydrothermal synthesis and calcination.

[8] In the above [7], the first template agent is cetyltrimethylamnmonium bromide, and the second template agent is tetrapropylammonium hydroxide.

[9] In the above [7] or [8], the catalyst is obtainable by performing the hydrothermal synthesis in the presence of a third template agent, followed by calcination.

[10] In the above [9], the third template agent is glycerol.

[11] A method for producing a catalyst for 1,3-butadiene synthesis for synthesizing 1,3-butadiene from ethanol, the method for producing a catalyst for 1,3-butadiene synthesis including: (i) mixing a zirconium alkoxide, an orthosilicic acid ester, and a first template agent for mesopore formation together with water to prepare a zirconium silicate precursor; (ii) mixing the zirconium silicate precursor, a zinc salt, an orthosilicic acid ester, and a second template agent for micropore formation together with water: (iii) performing hydrothermal synthesis using the resulting mixture; and (iv) calcining the reaction product resulting from the hydrothermal synthesis.

[12] In the above [11], the first template agent is cetyltrimethylammonium bromide, and the second template agent is tetrapropylammonium hydroxide.

[13] In the above [11] or [12], a third template agent for macropore formation is added to the mixture and mixed, and the hydrothermal synthesis is performed using the mixed solution containing the third template agent.

[14] hi the above [13], the third template agent is glycerol.

Advantageous Effects of Invention

According to embodiments of the invention. 1,3-butadiene can be efficiently synthesized from ethanol.

DESCRIPTION OF EMBODIMENTS

Figure 1:
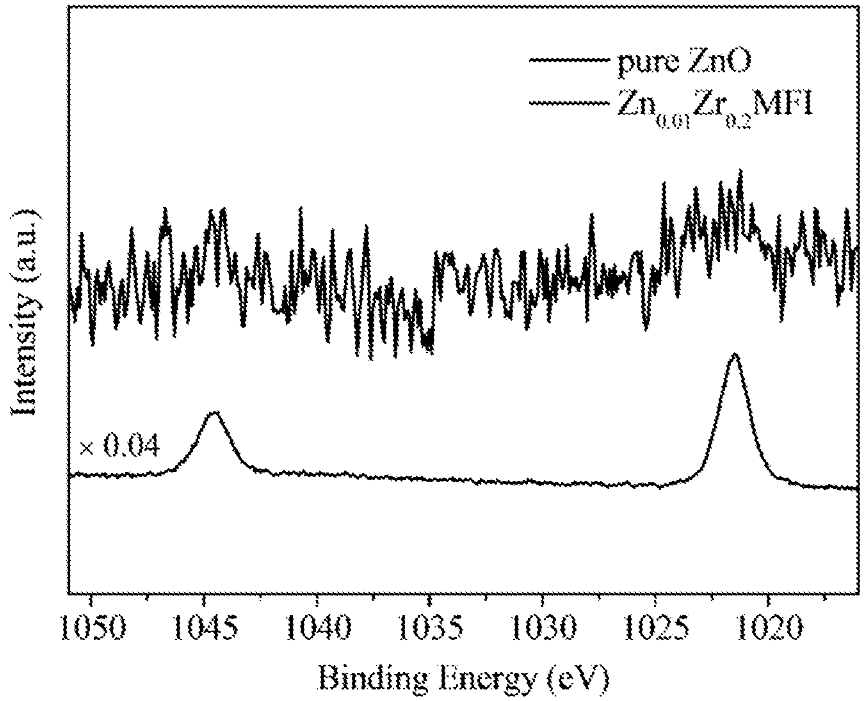
FIG. 1 shows the Z 2p spectra, of the ZnZrMFI catalyst of Example 1 and pure ZnO.

Hereinafter, a catalyst for 1,3-butadiene synthesis (hereinafter sometimes simply referred to as a "catalyst") according to this embodiment and a method for producing 1,3-butadiene using the same will be described.

[Catalyst for 1,3-Butadiene Synthesis]

A catalyst according to an embodiment is a catalyst for synthesizing 1,3-butadiene from ethanol and contains a porous silica support, Zn, and Zr.

The silica support is made of crystalline silica, which is porous crystalline with a three-dimensional pore structure. Therefore, compared to a structure composed of amorphous silica, the specific surface area is larger, which is advantageous for the dispersion of various active centers, allowing for an improvement in catalyst performance. As pores, micropores, mesopores, and macropores can be mentioned. In one embodiment, the silica support has micropores as well as mesopores and/or macropores. As used herein, "micropores" refer to pores having a pore size of 2 nm or less. "Mesopores" refer to pores having a pore size of more than 2 nm and less than 50 nm. "Macropores" refer to pores having a pore size of 50 nm or more.

The silica support has a framework structure containing $SiO_2$. The framework structure is basically composed of $SiO_2$, but Si contained in the framework structure may be partially substituted with a trivalent, tetravalent, and/or pentavalent element such as aluminum. It is preferable that the silica support has an $SiO_2$ framework structure without such substitution. As one embodiment, the silica support may be a zeolite containing no elemental aluminum (i.e., dealuminated zeolite).

The framework structure of the silica support is not particularly limited, and, for example, MFI type, BEA type, PER type, MWW type, MOR type, FAU type, LTA type, LTL type, and the like can be mentioned. The silica support may have one of them, or may also have a combination of two or more kinds of framework structures. Among them, a silica support in one embodiment preferably has an MEI-type framework structure.

In the above catalyst, zinc (Zn) is supported on the silica support in the form of an oxide, i.e., ZnO. Because the atomic radius of Zn is larger than that of Si, Zn does not enter the framework structure of the silica support in the course of catalyst synthesis, and is supported on the silica support in the form of an oxide. The ZnO supported on the silica support is believed to mainly promote the dehydrogenation of ethanol.

In the above catalyst, zirconium (Zr) is contained mainly in the state of having been interacted with silanol groups (Si—OH) of the silica support. Because the atomic radius of Zr is larger than that of Si, Zr does not enter the framework structure of the silica support in the course of catalyst synthesis. Zr interacts with silanol groups on the $SiO_2$ surface within pores of the silica support, forming Lewis active centers. Here, the interaction between silanol groups and Zr means the formation of any bond between silanol groups and Zr. Specifically, it is preferable that Zr coordinates with silanol groups, and Zr forms an Si—O—Zr bond with Si of the silanol groups. For example, it may take the form shown by the following formula (1), i.e., $Zr(OH)(OSi)_3$.

[Chemical formula 1]

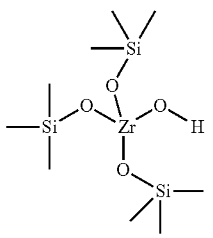

(1)

In the above catalyst, Zr may have entirely interacted with silanol groups as described above, but it is also possible that Zr is partially supported on the silica support in the form of an oxide, that is, $ZrO_2$. In a catalyst according to one embodiment, Zr may be contained in the form of $Zr(OH)(OSi)_3$ and $ZrO_2$.

The catalyst according to this embodiment has a multimodal pore size distribution with a first peak pore size ($D_{micro}$) of 2 nm or less and a second peak pore size ($D_{meso+macro}$) of more than 2 nm. A peak pore size refers to the pore size at which the distribution curve in a pore size distribution has a maximum value, and refers to the pore size at the top of a peak in the distribution curve. The catalyst according to this embodiment has a peak pore size on each side of 2 nm as the boundary. The peak pore size of 2 nm or less is referred to as the first peak pore size ($D_{micro}$), and the peak pore size of more than 2 urn is referred to as the second peak pore size ($D_{meso+macro}$). Such a multimodal pore size distribution is due to the fact that the catalyst has a structure containing micropores as well as mesopores and/or macropores (hereinafter also referred to as a "hierarchical structure"), and it is more preferable that the catalyst has a hierarchical structure containing micropores, mesopores, and macropores. As a result of having the hierarchical structure, the mass transfer efficiency and the resistance to carbon precipitation are improved, enhancing the stability of the catalyst.

$D_{micro}$ is not particularly limited as long as it is 2 nm or less as described above, but is preferably 0.2 nm or more and 1.5 nm or less, more preferably 0.3 nm or more and 1.0 nm or less, and still more preferably 0.4 nm or more and 0.8 nm or less.

$D_{meso+macro}$ is not particularly limited as long as it is more than 2 urn as described above, but is preferably 5 nm or more and 1,000 nm or less, more preferably 10 nm or more and 500 nm or less, still more preferably 20 nm or more and 300 nm or less, and yet more preferably 30 nm or more and 100 nm or less.

In the above catalyst, it is preferable that the micropore volume ($V_{micro}$) calculated by the t-plot method is 0.03 to 0.30 $cm^3/g$, and the mesopore volume ($V_{meso}$) calculated by the BJH method is 0.30 to 2.0 $cm^3/g$. As a result of having such a micropore volume ($V_{micro}$) and such a mesopore volume ($V_{meso}$), the effect produced by having a hierarchical structure can be further enhanced.

$V_{micro}$ is more preferably 0.04 to 0.20 $cm^3/g$, and still more preferably 0.05 to 0.10 $cm^3/g$. $V_{meso}$ is more preferably 0.40 to 1.0 $cm^3/g$, and still more preferably 0.50 to 0.80 $cm^3/g$.

In the above catalyst, the molar ratio Zn/Si of elemental zinc to elemental silicon is not particularly limited, but is preferably 0.001 to 0.1. When the molar ratio Zn/Si is 0.001 or more, the promoting effect on the dehydrogenation of ethanol can be enhanced. When the molar ratio Zn/Si is 0.1 or less, the dehydrogenation of ethanol can be promoted without inhibiting the action of other active species. The molar ratio Zn/Si is preferably 0.005 or more, and more preferably 0.008 or more. In addition, the molar ratio Zn/Si is preferably 0.05 or less, and more preferably 0.03 or less.

In the above catalyst, the molar ratio Zr/Si of elemental zirconium to elemental silicon is not particularly limited, but is preferably 0.05 to 0.5. When the molar ratio Zr/Si is 0.05 or more, the promoting effects on aldol condensation and MPV reduction can be enhanced. When the molar ratio Zr/Si is 0.5 or less, the generation of by-products can be suppressed. The molar ratio Zr/Si is preferably 0.08 or more, and more preferably 0.1 or more. In addition, the molar ratio Zr/Si is preferably 0.4 or less, and more preferably 0.3 or less.

[Method for Producing Catalyst for 1,3-Butadiene Synthesis]

The method for producing the above catalyst is not particularly limited, but preparation by a hydrothermal synthesis method is preferable, and preparation by a one-pot hydrothermal synthesis method is more preferable.

A production method using a hydrothermal synthesis method according to a preferred embodiment includes the following steps:

(i) a step of mixing a zirconium alkoxide, an orthosilicic acid ester, and a first template agent for mesopore formation together with water to prepare a zirconium silicate precursor;

(ii) a step of mixing the zirconium silicate precursor, a zinc salt, an orthosilicic acid ester, and a second template agent for micropore formation together with water;

(iii) a step of performing hydrothermal synthesis using the resulting mixture, and (iv) a step of calcining the reaction product resulting from the hydrothermal synthesis.

According to the production method including the above steps (i) to (iv), a multifunctional catalyst having various active centers such as a dehydrogenation site, a Lewis acid site, and a mild Bronsted site can be synthesized in one pot. In addition, the active centers can be uniformly dispersed, and, therefore, the interaction between the active centers can be promoted. In addition, a catalyst having a hierarchical structure can be synthesized, and, in particular, Zr can be interacted with silanol groups on the silica surface in hierarchical pores to form Lewis active centers.

As orthosilicic acid esters used as silica sources in steps (i) and (ii), for example, tetraethoxysilane (TEOS), tetramethoxysilane (TEMOS), tetrapropoxysilane, tetrabutoxysilane, and the like can be mentioned. One of them may be used alone, and it is also possible to use a combination of two or more kinds.

Zirconium alkoxides are not particularly limited, and, for example, zirconium methoxide, zirconium ethoxide, zirconium propoxide, zirconium butoxide, and the like can be mentioned. One of them may be used alone, and it is also possible to use a combination of two or more kinds.

The first template agent is not particularly limited as long as it is a template agent capable of forming mesopores, but it is preferable to use cetyltrimethylammmonium bromide (CTAB).

Zinc salts are not particularly limited, and, for example, water-soluble zine salts such as zinc acetate, zinc nitrate, zinc sulfate, zinc chloride, and zinc bromide can be mentioned. One of them may be used alone, and it is also possible to use a combination of two or more kinds.

The second template agent is not particularly limited as long as it is a template agent capable of forming micropores, but it is preferable to use tetrapropylammonium hydroxide (TPAOH), for example.

Step (i) is a step of synthesizing a zirconium silicate precursor. As a result of the hydrolysis of an orthosilicic acid ester and a zirconium alkoxide in the presence of a first template agent for mesopore formation, a mesoporous precursor can be synthesized. Incidentally, in step (i), when a zirconium alkoxide, an orthosilicic acid ester, a first template agent, and water are mined, other components such as lower alcohols may also be contained. In addition, the zirconium silicate precursor is not calcined in step (i)

More specifically, in step (i), it is possible that a zirconium alkoxide and an orthosilicic acid ester are dissolved in a lower alcohol such as ethanol, the resulting solution is mixed with a first template agent and water, and the resulting first mixture is aged. As a result of aging, the orthosilicic acid ester hydrolyzes and undergoes dehydration condensation in the presence of the first template, while the zirconium alkoxide hydrolyzes, and Zr interacts with silanol groups, producing a mesoporous precursor. Subsequently, centrifugation and drying are performed, thereby giving a powdery zirconium silicate precursor.

The amount of orthosilicic acid ester used in step (i) is not particularly limited, but is preferably 30 to 70 mass %, more preferably 40 to 60 mass %, of the total amount of orthosilicic acid ester used in steps (i) and (ii).

The amount of zirconium alkoxide used is not particularly limited, but is preferably such that, relative to the total amount of orthosilicic acid ester used in steps i) and (ii), the molar ratio Zr/Si of elemental zirconium to elemental silicon is 0.05 to 0.5, more preferably 0.08 to 0.4, and still more preferably 0.1 to 0.3.

The amount of first template agent used is not particularly limited and may be 10 to 80 parts by mass, or 20 to 40 parts by mass, per 100 parts by mass of the total amount of orthosilicic acid ester used in steps (i) and (ii).

In step (ii), using the zirconium silicate precursor obtained in step (i), a second template agent is added together with an additional silica source to synthesize a second precursor.

More specifically, in step (ii), it is possible that a zinc salt and an orthosilicic acid ester are dissolved in a lower alcohol such as ethanol, while a zirconium silicate precursor is added and mixed, and a second template agent and water are added to the resulting mixed solution and mixed. As a result, the orthosilicic acid ester hydrolyzes and undergoes dehydration condensation in the presence of the zinc salt, the zirconium silicate precursor, and the second template agent, producing a ZnZr silicate precursor.

The amount of zinc salt used is not particularly limited, but is preferably such that, relative to the total amount of orthosilicic acid ester used in the steps (i) and (ii), the molar ratio Zn/Si of elemental zinc to elemental silicon is 0.001 to 0.1, more preferably 0.005 to 0.05, and still more preferably 0.008 to 0.03.

The amount of second template agent used is not particularly limited and may be 50 to 130 parts by mass, or 80 to 100 parts by mass, per 100 parts by mass of the total amount of orthosilicic acid ester used in steps i) and (ii).

In step (ii), the lower alcohol may be distilled off from the ZnZr silicate precursor-containing mixture thus obtained.

Subsequently, the hydrothermal synthesis of step (iii) may be performed immediately, but a third template agent may also be added before the hydrothermal synthesis. That is, in one embodiment, it is possible that a third template agent for macropore formation is added to the ZnZr silicate precursor-containing mixture and mixed, and the hydrothermal synthesis of step (iii) is performed using the mixed solution containing the third template agent. As a result of adding a third template agent, larger macropores can be formed.

The third template agent is not particularly limited as long as it is a template agent capable of forming macropores, but it is preferable to use glycerol, for example. Hydrothermal synthesis in the presence of glycerol can significantly reduce the catalyst particle size, which is advantageous for improving the mass transfer efficiency.

The amount of third template agent used is not particularly limited and may be 10 to 80 parts by mass, or 30 to 50 parts by mass, per 100 parts by mass of the total amount of orthosilicic acid ester used in steps (i) and (ii).

In step (iii), hydrothermal synthesis is performed using the mixture obtained in the above step (ii). Hydrothermal synthesis is a reaction performed in the presence of high-temperature, high-pressure hot water, and further dehydration condensation takes place to produce silica. At this time, because of the presence of the first template agent and the second template agent (preferably further the third template agent), pores having pore sizes corresponding to the respective template agents are formed, forming a hierarchical structure. In addition, because one-pot hydrothermal synthesis is performed, the active centers Zn and Zr can be uniformly dispersed in the silica support, promoting the interaction between active centers.

Hydrothermal synthesis can be performed using an autoclave, for example. The treatment conditions are not particularly limited, and the treatment may be performed, for example, at 150 to 180° C. for 24 to 96 hours under a pressure spontaneously generated due to volume expansion.

After the hydrothermal synthesis, the resulting reaction product is dried, and then, in step (iv), the reaction product is calcined. As a result, a catalyst according to one embodiment is obtained. The calcination temperature is not particularly limited and may be, for example, 300 to 700° C., or 400 to 600° C. If necessary, calcination may be followed by pulverization and further molding, such as particle sizing.

[Method for Producing 1,3-Butadiene]

The method for producing 1,3-butadiene according to this embodiment includes obtaining 1,3-butadiene from ethanol in the presence of the catalyst according to this embodiment described above. For this purpose, a raw material containing ethanol needs to be brought into contact with the above catalyst.

The synthesis route from ethanol to 1,3-butadiene using the catalyst is not particularly limited, but is generally believed to be as follows. That is, (1) ethanol undergoes dehydrogenation to form acetaldehyde, (2) acetaldehyde undergoes aldol condensation to form acetaldol, (3) acetaldol undergoes a dehydration reaction to form crotonaldehyde, (4) crotonaldehyde undergoes MPV reduction together with ethanol to form crotyl alcohol, and (5) crotyl alcohol undergoes dehydration to form 1,3-butadiene.

The ethanol used in the production is not particularly limited and may be, for example, bioethanol produced from biomass, or may also be ethanol synthesized through a hydration reaction of fossil fuel-derived ethylene, etc. In addition to ethanol, the above raw material may also contain other components such as acetaldehyde.

The method for bringing a raw material containing ethanol into contact with the catalyst is not particularly limited as long as the method can convert ethanol into 1,3-butadiene in the presence of the catalyst, and the contact may be made in the gas phase or in the liquid phase. It is preferable that the raw material containing ethanol is used as a gas, and the gas is passed through a catalyst bed containing the catalyst to cause a reaction in the gas phase.

When the reaction is performed in the gas phase, the raw material gas may be fed to the reaction system without being diluted, or also may be fed after being diluted with an inert gas such as nitrogen or argon.

The reaction temperature (catalyst bed temperature) is not particularly limited as long as it is a temperature that can convert ethanol into 1,3-butadiene, and may be, for example, 250 to 500° C., or 300 to 400° C. The reaction pressure is not particularly limited either and may be, for example, from atmospheric pressure to 1 MPa.

The reaction mode may be a continuous flow type or a batch type. In the case of a continuous flow type, the weight hourly space velocity (WHSV), which is the ratio of the raw material feed rate (weight/hour) to the catalyst weight, is not particularly limited and may be, for example, 0.1 to 10 $h^{-1}$, or 0.3 to 2 $h^{-1}$.

The reaction form is not particularly limited and may be a fixed-bed type, a moving-bed type, or a fluidized-bed type. The form of the reactor is not particularly limited either, and tubular reactors and the like can be used, for example.

After the reaction, the obtained product may be subjected to purification, such as distillation, if necessary. As a result, unreacted ethanol and by-products such as ethylene, ether, and acetaldehyde can be removed.

EXAMPLES

Examples will be shown hereinafter, but the invention is not limited to these examples.

Example 1: Preparation of ZnZrMFI Catalyst 2.60 g of tetraethoxysilane (TEOS) and 240 g of zirconium butoxide ($Zr(OBu)_4$) were added to 10 mL of ethanol and dissolved by stirring. The resulting solution was added to an aqueous solution of 1.91 g of cetyltrimethylammonium bromide (CTAB) dissolved in 300 mL of water and aged overnight. Subsequently, the solution was centrifuged and dried at 100° C. for 12 hours, thereby giving a zirconium silicate precursor.

0.05 g of zinc acetate ($Zn(CH_3COO)_2 \cdot 2H_2O$) and 2.61 g of TEOS were added to 10 mL of ethanol and dissolved by stirring for 1 hour. 1.00 g of the zirconium silicate precursor was added thereto and stirred for 1 hour, and then 5.08 g of tetrapropylammonium hydroxide (TPAOH) and 18.69 g of water were added and mixed by stirring for 4 hours. The resulting mixture was heated at 90° C. for 4 hours to distill off ethanol, and then 2.30 g of glycerol was added and mixed. Next, the mixture was transferred to a fluorine resin-lined stainless steel autoclave and subjected to a hydrothermal synthesis reaction at 130° C. for 48 hours under a pressure spontaneously generated due to volume expansion. The resulting reaction product was dried at 100° C. for 12 hours and then calcined in air at 550° C. for 5 hours, thereby giving a ZnZrMFI catalyst (molar ratio Zn/Si=0.01, molar ratio Zr/Si=0.2).

Using an apparatus called "ESCALAB 250Xi" manufactured by Thermo Fisher Scientific, the obtained ZnZrMFI catalyst was subjected to X-ray photoelectron spectroscopy (XPS) analysis using an Al Ka X-ray source. As a result, the Zn 2p spectrum shown in FIG. 1 and the Zr 3d spectrum shown in FIG. 2 were obtained. In addition, the crystal structure of the ZnZrMFI catalyst was analyzed using the X-ray diffraction (XRD) method (CuKα 40 kV, 20 mA, 6° to 60°), and the measurement results shown in FIG. 3 were obtained.

Figure 2:
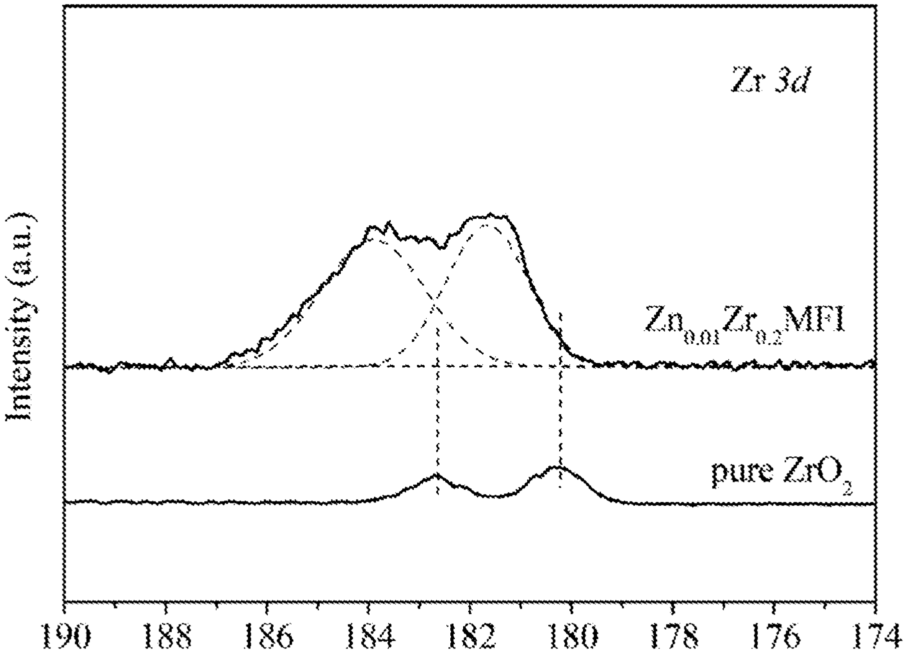
FIG. 2 shows the Zr 3d spectra of the ZnZrMFI catalyst of Example 1 and pure $ZrO_2$.
Figure 6:
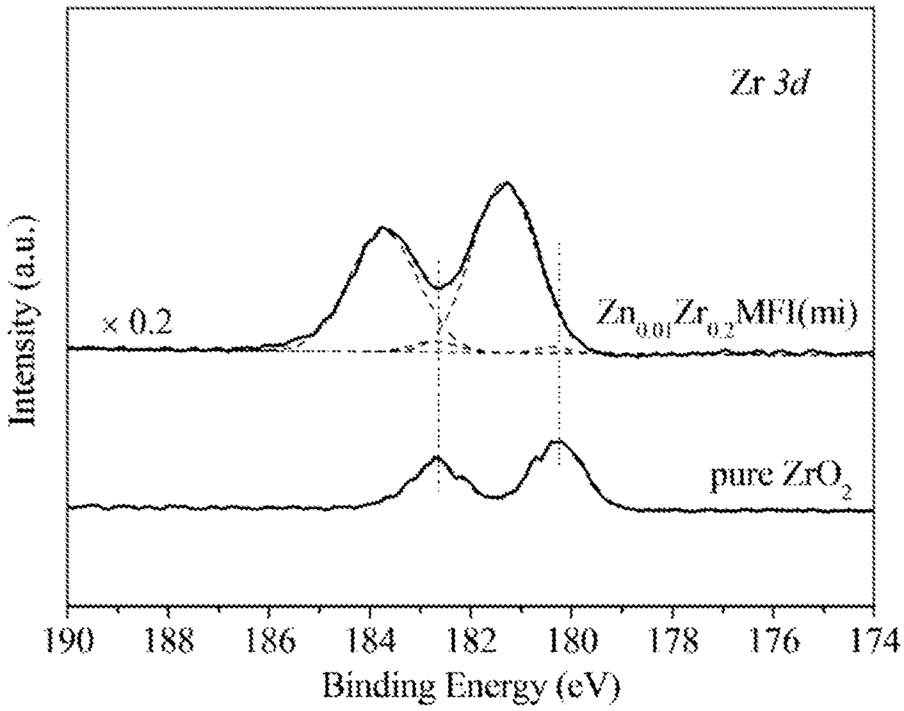
FIG. 6 shows the Zr 3d spectra of the catalyst of Comparative Example 3 and pure $ZrO_2$

With respect to the binding energies of the Zr 3d peaks shown in FIG. 2, two peaks were observed for pure $ZrO_2$. Meanwhile, for the ZnZrMFI catalyst ($Zn_{0.01}Zr_{0.2}MFI$), the binding energies of the Zr 3d peaks have shifted to the high energy side compared to pure $ZrO_2$, indicating that Zr and silanol groups have interacted to form an Si—O—Zr bond. FIG. 6 shows the Zr 3d spectrum of the catalyst of Comparative Example 3 ($Zn_{0.01}Zr_{0.2}MFI(mi)$), which will be described later, together with the Zr 3d spectrum of pure $ZrO_2$. The two peaks of the catalyst of Comparative Example 3 can be divided into two main peaks corresponding to Si—O—Zr and two weak peaks corresponding to $ZrO_2$. From this, it can be seen that the synthesis method using a zirconium silicate precursor according to Example 1 can further strengthen the interaction between Zr and silanol groups and can further suppress the production of $ZrO_2$.

With respect to the binding energies of the Zn 2p peaks shown in FIG. 1, there is no obvious change in the peaks of the ZnZrMFI catalyst ($Zn_{0.01}Zr_{0.2}MFI$) compared to pure ZnO, showing the presence in the form of ZnO.

Figure 3:
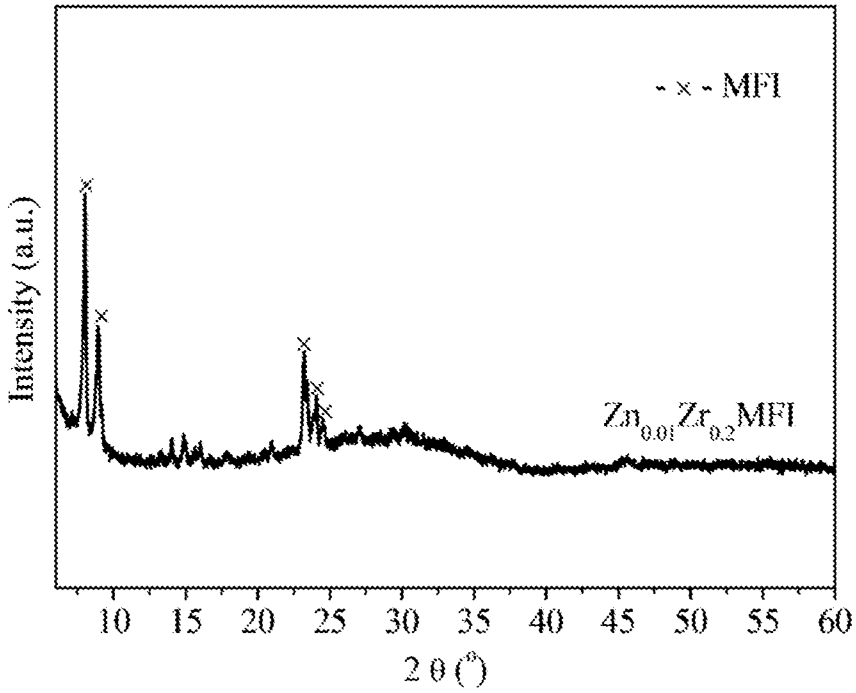
FIG. 3 is a graph showing the XRD measurement results of the ZnZrMFI catalyst of Example 1.

In addition, as shown in FIG. 3, the ZnZrMFI catalyst ($Zn_{0.01}Zr_{0.2}MFI$) has peaks peculiar to MFI, which are indicated by "x".

From the above, it can be seen that the prepared ZnZrMFI catalyst contains a silica support having an MFI-type framework structure, Zn is supported on the silica support in the form of ZnO, and Zr is contained in the form of $Zr(OH)(OSi)_3$.

Comparative Example 1: Preparation of ZnCe/Beta Catalyst 100 mL of 13 mol/L nitric acid was added to 5.0 g of H-beta ("941HOA" manufactured by Tosoh Corporation), stirred at 100° C. for 12 hours, then filtered, and washed to give Si-beta. 5 g of Si-beta, 0.96 g of $Zn(NO_3)_2 \cdot 6H_2O$, and 0.66 g of $Ce(NO_3)_3 \cdot 6H_2O$ were nixed, pulverized, and then calcined in air at 500° C. for 6 hours. As a result, a ZnCe/beta catalyst (Zn content=5.0 mass %, Ce content=5.0 mass %) was obtained.

Comparative Example 2: Preparation of ZrMFI Catalyst 1.91 g of CTAB was dissolved in 300 mL of deionized water with stirring to give a solution A. 2.60 g of TEOS and 2.40 g of $Zr(OBu)_4$ were mixed with 10 mL of ethanol under stirring to give a solution B. The solution B was slowly added to the solution A with stirring and aged overnight. The solid product was centrifuged at 2,500 rpm and dried at 60° C. overnight to give a zirconium silicate precursor.

2.60 g of TEOS was added to 10 mL of ethanol to prepare a mixed solution. The zirconium silicate precursor was added to the mixed solution and stirred for 1 hour. Next, 5.08 g of TPAOH and 18.69 g of $H_2O$ were added dropwise to the mixed solution with stirring. The mixed solution was stirred at 700 rpm continuously for 4 hours and then heated at 90° C. for 4 hours to remove most of water and ethanol from the mixture. The formed gel was mixed with 2.30 g of glycerol, then transferred to a fluorine resin-lined stainless steel autoclave, and subjected to hydrothermal synthesis at 130° C. for 48 hours. The product was dried at 100° C. for 12 hours and then calcined in air at 550° C. for 5 hours to give a $Zr_{0.2}MFI$ catalyst.

Comparative Example 3: Preparation of ZnZrMFI(mi) Catalyst 0.05 g of $Zn(CH_3COO)_2 \cdot 2H_2O$ and 5.21 g of TEOS were added to 10 mL of ethanol and dissolved by stirring for 1 hour. 2.40 g of $Zr(OBu)_4$ was added thereto and stirred for 1 hour, and then 5.08 g of TPAOH and 18.69 g of water were added and mixed by stirring for 4 hours. The resulting mixture was heated at 90° C. for 4 hours to distill off ethanol, then transferred to a fluorine resin-lined stainless steel autoclave, and subjected to a hydrothermal synthesis reaction at 130° C. for 48 hours under a pressure spontaneously generated due to volume expansion. The resulting reaction product was dried at 100° C. for 12 hours and then calcined in air at 550° C. for 5 hours, thereby giving a ZnZrMFI(mi) catalyst (molar ratio Zn/Si=0.01, molar ratio Zr/Si=0.2).

[Measurement of Pore Size and Pore Volume]

With respect to the ZnZrMFI catalyst of Example 1 and the ZnZrMFI(mi) catalyst of Comparative Example 3, pore size was measured, and, from the pore size distribution, the peak pore sizes ($D_{micro}$, $D_{meso+macro}$) were determined. In addition, as pore volume, the micropore volume ($V_{micro}$) and the mesopore volume ($V_{meso}$) were determined. The measurement methods are as follows.

Using a catalyst as the sample, nitrogen ($N_2$) adsorption/desorption was measured using "3Flex 2MP" manufactured by Micromeritics as the measuring apparatus. Incidentally, prior to the measurement, the sample was degassed under vacuum at 350° C. for 5 hours.

Figure 4:
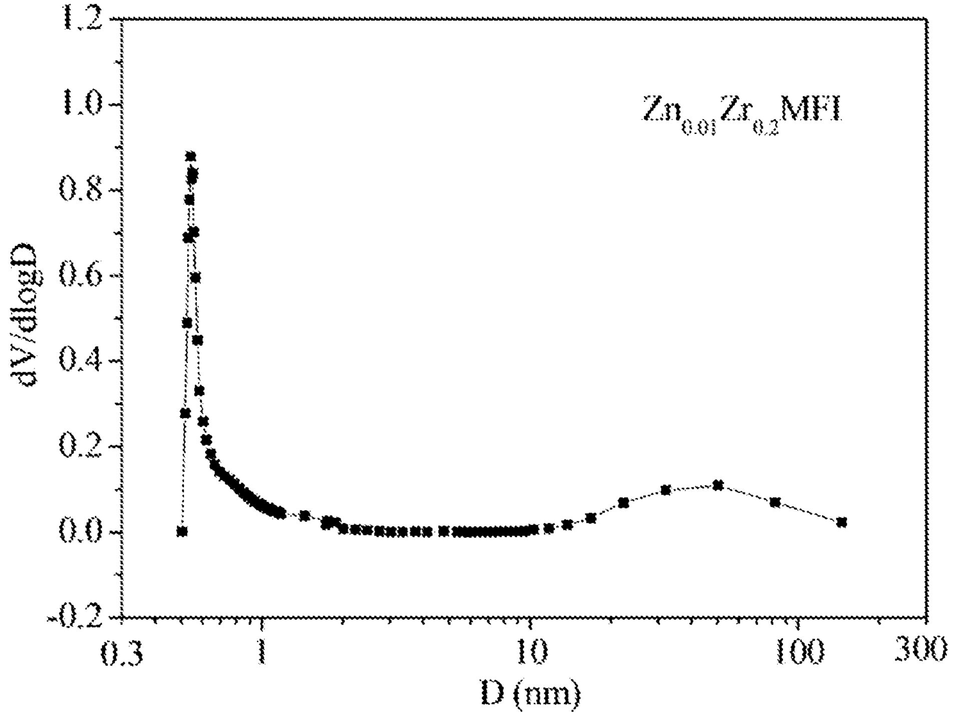
FIG. 4 is a graph showing the pore size distribution of the catalyst of Example 1.

This measuring apparatus analyzes the pore size distribution of micropores by the HK method, while analyzes the pore size distribution of mesopores and that of macropores by the BJH method. The pore size distribution of the Log differential pore volume distribution (dV/d log D) was determined by the measurement. As shown in FIG. 4, this pore size distribution has pore size on the horizontal axis and dV/d log D on the vertical axis. dV/d log D is the value obtained by dividing the differential pore volume dV by the difference value d(log D) as the logarithmic pore size, and is plotted against average pore size for each section. From the obtained pore size distribution, the peak pore size of micropores ($D_{micro}$) and the peak pore size of mesopores and macropores ($D_{meso+macro}$) were determined.

In addition, the micropore volume ($V_{micro}$) was calculated by the t-plot method, and the mesopore volume ($V_{meso}$) was calculated by the BJH method.

Figure 5:
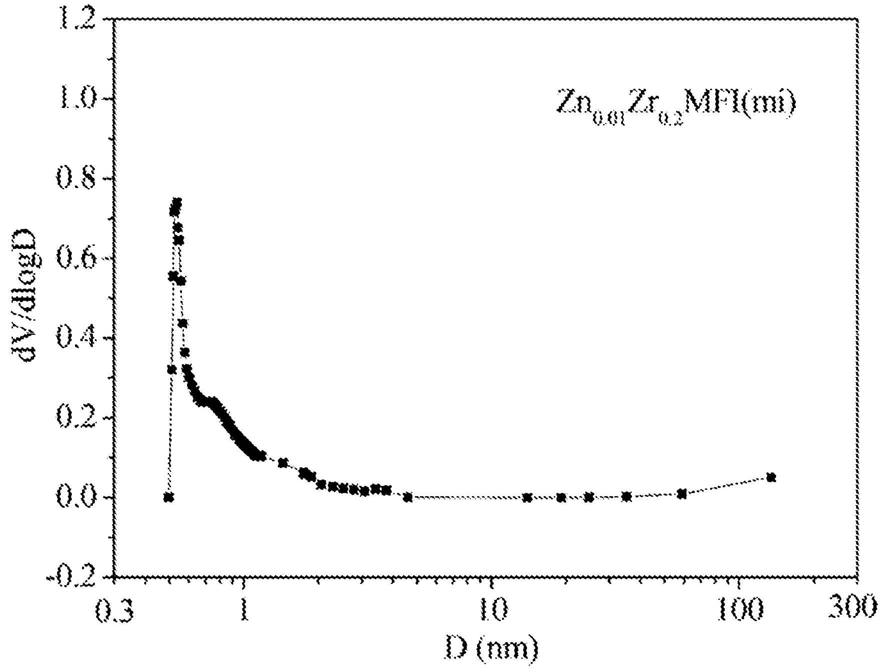
FIG. 5 is a graph showing the pore size distribution of the catalyst of Comparative Example 3.

The pore size distributions of the catalysts of Example 1 and Comparative Example 3 are shown in FIGS. 4 and 5, respectively. As shown in FIG. 5, the catalyst of Comparative Example 3 had a single peak pore size at $D_{micro}$=0.54 nm. In contrast, as shown in FIG. 4, the catalyst of Example 1 had two peak pore sizes at $D_{micro}$=0.55 nm and at $D_{meso+macro}$=50.18 nm, that is, had a multimodal pore size distribution. In addition, the catalyst of Example 1 had micropores with a pore size of 2 nm or less, mesopores with a pore size of more than 2 nm and less than 50 nm, and macropores with a pore size of 50 nm or more, that is, had hierarchical nano-sized pores.

In addition, as shown in Table 1, compared to the catalyst of Comparative Example 3, the catalyst of Example 1 had a large mesopore volume $V_{meso}$, and the total pore volume $V_{total}$ combined with the micropore volume $V_{micro}$ was also large.

[Catalyst Performance Evaluation Test]

Each catalyst prepared above was subjected to a catalyst performance evaluation test through a 1,3-butadiene synthesis reaction from ethanol. The synthesis reaction was performed under atmospheric pressure using a fixed-bed flow reactor made of quartz with an inner diameter of 4 mm.

Figure 7:
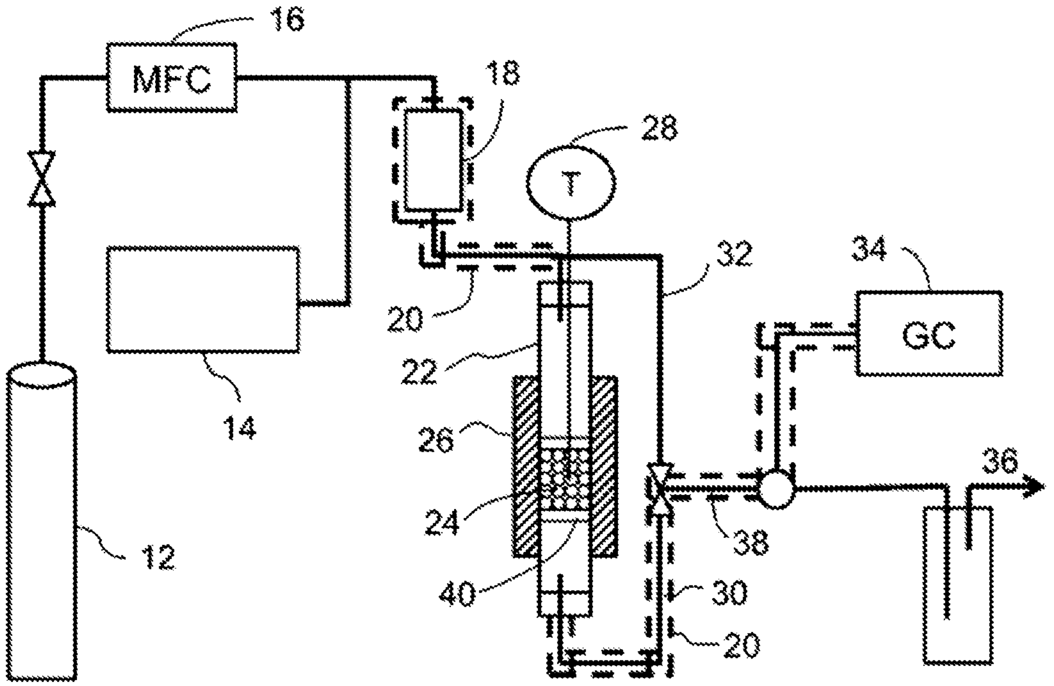
FIG. 7 is a conceptual diagram of the reaction apparatus used in the Examples.

The conceptual diagram of the reaction apparatus is as shown in FIG. 7. In FIG. 7, reference numeral 12 indicates a nitrogen cylinder that feeds nitrogen as a carrier gas, reference numeral 14 indicates a syringe pump that feeds ethanol, reference numeral 16 indicates a mass flow controller (MFC), reference numeral 18 indicates an evaporator; and reference numeral 20 indicates a ribbon heater for line heating, which heats the outer periphery of a tube through which the gas flows.

Reference numeral 22 indicates a fixed-bed flow-type reactor, reference numeral 24 indicates a catalyst bed in the reactor 22, reference numeral 26 indicates an electric furnace that heats the reactor 22, and reference numeral 28 indicates a thermocouple thermometer (TC) that detects the temperature of the catalyst bed 24.

Reference numeral 30 indicates a tube through which the gas that has passed through the reactor 22 flows, reference numeral 32 indicates a bypass route that bypasses the reactor 22, reference numeral 34 indicates a gas chromatograph (GC) for analyzing gas products, reference numeral 36 indicates an exhaust gas outlet, and reference numeral 38 indicates a six-way valve for switching the flow path for the tube 30, the bypass route 32, the GC 34, and the exhaust gas outlet 36.

0.5 g of a catalyst was packed in the reactor 22 to form a catalyst bed 24, and the catalyst bed 24 was filled with quartz wool 40 at both ends and fixed. Nitrogen was passed from the nitrogen cylinder 12 through the MFC 16 into the reactor 22 at a flow rate of 20 mL/min to perform a pretreatment at 400° C. for 1 hour. After cooling to 350° C., ethanol was introduced into the reaction system using the syringe pump 14 at a rate of 0.24 mL/h (diluted with nitrogen passed as a carrier gas at 20 mL/min) (WHSV=0.38 $h^{-1}$). The catalyst was evaluated for 6 hours.

The gas product emitted from the reactor 22 was introduced to the gas chromatograph (GC) 34 on line, and the gas products were analyzed using a gas chromatograph ("Shimadzu GC-14B" manufactured by Shimadzu Corporation and "DR-1 Column (30 m×0.25 mm×0.25 μm)" manufactured by GL Sciences) and a flame ionization detector (FID).

The calculation formulas for the conversion (ethanol conversion), selectivity of each product, and yield (yield of 1,3-butadiene) are shown below.

$$\text{Conversion } (\%) = \frac{n_{Ethanol,in} - n_{Ethanol,out}}{n_{Ethanol,in}} \times 100 \quad \text{[Equation 1]}$$

$$\text{Selectivity } (\%) = \frac{A_{ri} \cdot f_{im}}{\sum_i A_{ri} \cdot f_{im}}$$

$n_{Ethanol,in}$ and $n_{Ethanol,out}$ in the formula represent the mole fractions of ethanol before and after the reaction, respectively. $A_{ri}$ and $f_{im}$ represent the chromatographic area ratio and the mass correction factor, respectively.

$$\text{Yield } (\%) = \text{conversion } (\%) \times 1,3\text{-butadiene selectivity } (\%)/100$$

TABLE 1

| | Conversion (%) | Selectivity (%) | | | | | Yield (%) | $V_{micro}$ ($cm^3/g$) | $V_{meso}$ ($cm^3/g$) | $V_{total}$ ($cm^3/g$) | $D_{micro}$ (nm) | $D_{meso+macro}$ (nm) |
|---|---|---|---|---|---|---|---|---|---|---|---|---|
| | | $C_4H_6$ | $C_2H_4$ | $CH_3CHO$ | Diethyl ether | Others | | | | | | |
| Comp. Ex. 1: ZnCe/beta | 51.1 | 65.8 | 6.7 | 7.3 | 16.2 | 4.1 | 33.6 | — | — | — | — | — |
| Comp. Ex. 2: ZrMFI | 30.1 | 1.7 | 54.5 | 3.0 | 40.7 | 0.0 | 0.5 | — | — | — | — | — |
| Comp. Ex. 3: ZnZrMFI(mi) | 97.9 | 38.7 | 28.1 | 4.6 | 5.1 | 23.5 | 37.9 | 0.09 | 0.36 | 0.45 | 0.54 | — |
| Ex. 1: ZnZrMFI | 89.8 | 61.4 | 9.0 | 11.9 | 4.7 | 10.9 | 55.1 | 0.07 | 0.56 | 0.63 | 0.55 | 50.18 |

The results are as shown in Table 1; 1,3-butadiene, ethylene, acetaldehyde, diethyl ether, and other coupling products were detected. With the catalyst of Example 1, compared to the ZnCe/beta catalyst of Comparative Example 1 and the ZnMFI catalyst of Comparative Example 2, the conversion of ethanol was significantly high, and the yield of 1,3-butadiene significantly improved. In addition, compared to Comparative Example 3, which is a ZnZrMFI (mi) catalyst having no hierarchical structure, the selectivity of 1,3-butadiene was significantly high, and the yield of 1,3-butadiene also significantly improved. Therefore, according to Example 1, efficient synthesis of 1,3-butadiene was possible.

[Catalyst Stability Test]

In the catalyst stability test, the catalyst of Example 1 was subjected to the catalyst performance evaluation test described above over 80 hours, and the conversion (Ethanol conv.) and 1,3-butadiene selectivity (Butadiene sel.) were measured every hour during the day.

Figure 8:
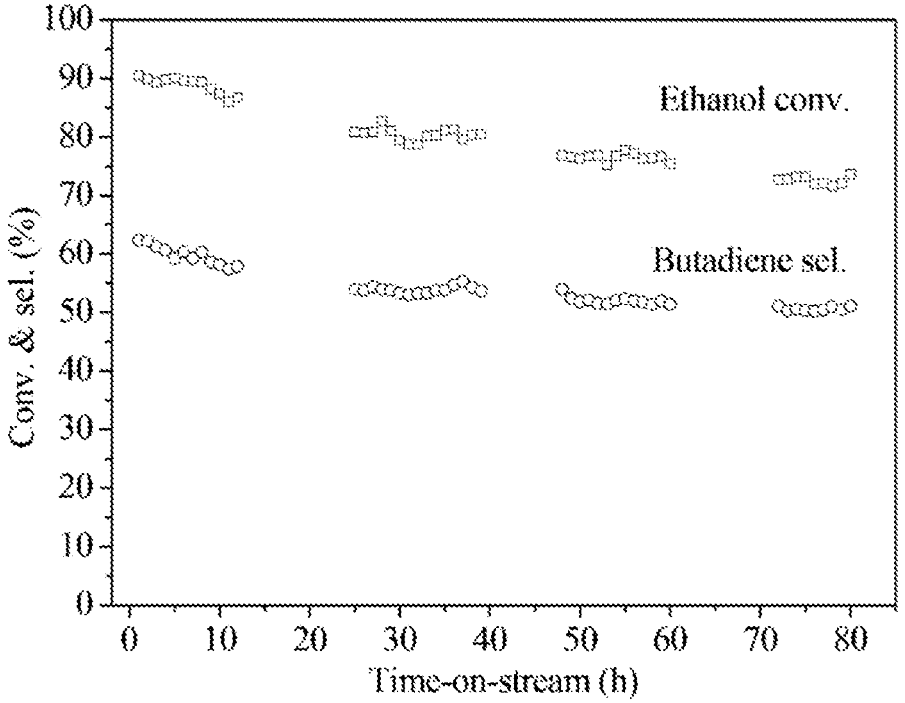
FIG. 8 is a graph showing the stability test results of the catalyst of Example 1.

The results are as shown in FIG. 8, and the catalyst of Example 1 had excellent stability.

Incidentally, with respect to the various numerical ranges described herein, the upper and lower limits thereof can be arbitrarily combined, and all such combinations are incorporated herein as preferred numerical ranges. In addition, the description of a numerical range "X to Y" means X or more and Y or less.

Although some embodiments of the invention have been described above, these embodiments are presented as examples and not intended to limit the scope of the invention. These embodiments can be implemented in other various modes, and, without departing fi-om the gist of the invention, various omissions, substitutions, and changes can be made thereto. These embodiments, as well as omissions, substitutions, and changes thereto, etc., fall within the scope and gist of the invention, and also fall within the scope of the claimed invention and its equivalents.

The invention claimed is:

1. A catalyst for 1,3-butadiene synthesis for synthesizing 1,3-butadiene from ethanol, comprising a porous silica support made of crystalline silica, Zn, and Zr, the catalyst having a multimodal pore size distribution with a first peak pore size ($D_{micro}$) of 2 nm or less and a second peak pore size ($D_{meso+macro}$) of more than 2 nm, wherein the multimodal pore size distribution refers to a distribution of pore diameters determined from nitrogen adsorption/desorption measurements, and wherein at least part of the Zr is bonded to silanol groups on a surface of the silica support within pores thereof, such that the Zr does not substitute for silicon atoms in a framework structure of the silica support.

2. The catalyst for 1,3-butadiene synthesis according to claim 1, comprising, as the Zn, ZnO supported on the silica support.

3. The catalyst for 1,3-butadiene synthesis according to claim 1, wherein the micropore volume ($V_{micro}$) calculated by the t-plot method is 0.03 to 0.30 $cm^3/g$, and the mesopore volume ($V_{meso}$) calculated by the BJH method is 0.30 to 2.0 $cm^3/g$.

4. The catalyst for 1,3-butadiene synthesis according to claim 1, wherein the silica support has an MFI-type framework structure.

5. The catalyst for 1,3-butadiene synthesis according to claim 1, wherein the molar ratio of Zn to Si is 0.001 to 0.1, and the molar ratio of Zr to Si is 0.05 to 0.5.

6. The catalyst for 1,3-butadiene synthesis according to claim 1, being a catalyst obtainable by mixing a zirconium alkoxide, an orthosilicic acid ester, and a first template agent together with water to prepare a zirconium silicate precursor, and mixing the zirconium silicate precursor, a zinc salt, an orthosilicic acid ester, and a second template agent together with water, followed by hydrothermal synthesis and calcination.

7. The catalyst for 1,3-butadiene synthesis according to claim 6, wherein the first template agent is cetyltrimethylammonium bromide, and the second template agent is tetrapropylammonium hydroxide.

8. The catalyst for 1,3-butadiene synthesis according to claim 6, wherein the catalyst is obtainable by performing the hydrothermal synthesis in the presence of a third template agent, followed by calcination.

9. The catalyst for 1,3-butadiene synthesis according to claim 8, wherein the third template agent is glycerol.

10. The catalyst for 1,3-butadiene synthesis according to claim 1, comprising, as the Zn, ZnO supported on the silica support, wherein at least part of the Zr is coordinated to silanol groups of the silica support through formation of at least one Si—O—Zr bond.

11. The catalyst for 1,3-butadiene synthesis according to claim 1, comprising, as the Zn, ZnO supported on the silica support, wherein at least part of the Zr has a coordination structure represented by $Zr(OH)(OSi)_3$.

12. The catalyst for 1,3-butadiene synthesis according to claim 1, wherein the multimodal pore size distribution is a pore size distribution of the Log differential pore volume distribution (dV/d log D) including a first mode and a second mode, the first peak pore size ($D_{micro}$) is a peak of the first mode of 2 nm or less, and the second peak pore size ($D_{meso+macro}$) is a peak of the second mode of 20 nm or more.

13. The catalyst for 1,3-butadiene synthesis according to claim 11, wherein the peak of the second mode of 30 nm or more.

* * * * *